United States Patent [19]

Smyth

[11] 4,452,622

[45] Jun. 5, 1984

[54] METHOD OF MAKING HIGHLY REACTIVE ION-LEACHABLE GLASS

[75] Inventor: Harold T. Smyth, East Brunswick, N.J.

[73] Assignee: Johnson & Johnson, New Brunswick, N.J.

[21] Appl. No.: 476,164

[22] Filed: Mar. 17, 1983

Related U.S. Application Data

[62] Division of Ser. No. 203,761, Nov. 7, 1980, Pat. No. 4,401,773.

[51] Int. Cl.³ .................. C08K 3/40; A61K 5/00; C03B 37/06
[52] U.S. Cl. .............................. 65/2; 65/5; 106/35; 260/998.11; 523/116
[58] Field of Search ............... 65/2, 5; 106/35; 260/998.11; 523/116

[56] References Cited

U.S. PATENT DOCUMENTS

| | | | |
|---|---|---|---|
| 2,714,662 | 8/1955 | McMullen | 65/2 |
| 3,265,478 | 8/1966 | Slayter | 65/2 |
| 3,814,717 | 6/1974 | Wilson et al. | 260/42.13 |
| 4,026,478 | 5/1977 | Albert et al. | 65/2 X |
| 4,089,830 | 5/1978 | Tezuka et al. | 260/29.65 |
| 4,123,416 | 10/1978 | Potter et al. | 260/42.18 |
| 4,143,018 | 3/1979 | Crisp et al. | 106/52 |
| 4,157,907 | 6/1979 | Kroyer | 427/221 |
| 4,174,334 | 11/1979 | Bertenshaw et al. | 260/29.6 M |
| 4,217,264 | 8/1980 | Mabie et al. | 260/998.11 |
| 4,250,277 | 2/1981 | Maries et al. | 260/998.11 |
| 4,271,057 | 6/1981 | Drake et al. | 260/998.11 |

FOREIGN PATENT DOCUMENTS

| | | |
|---|---|---|
| 1504520 | 3/1978 | United Kingdom . |
| 2012773 | 8/1979 | United Kingdom . |
| 1554553 | 10/1979 | United Kingdom . |
| 1554554 | 10/1979 | United Kingdom . |
| 1554555 | 10/1979 | United Kingdom . |

OTHER PUBLICATIONS

Barry et al., J. Dent. Res. 58 (3), pp. 1072–1079, (1979).
Wilson et al., J. Dent. Res. 58 (3), pp. 1065–1071, (1979).

Primary Examiner—Robert L. Lindsay, Jr.
Attorney, Agent, or Firm—Jason Lipow

[57] ABSTRACT

A method is provided for producing a highly reactive, ion-leachable glass for cement compositions. The method contemplates blending together a mixture of ion-leachable, inorganic compositions, forming the blended mixtures into shaped charges, heating the shaped charges to form a homogeneous melt, and finally blowing, in a gaseous mixture, to form partially solidified thin glass fibers. The method uniquely produces glass having a degree of crystallinity of less than 1 percent by weight in crystalline form.

9 Claims, 1 Drawing Figure

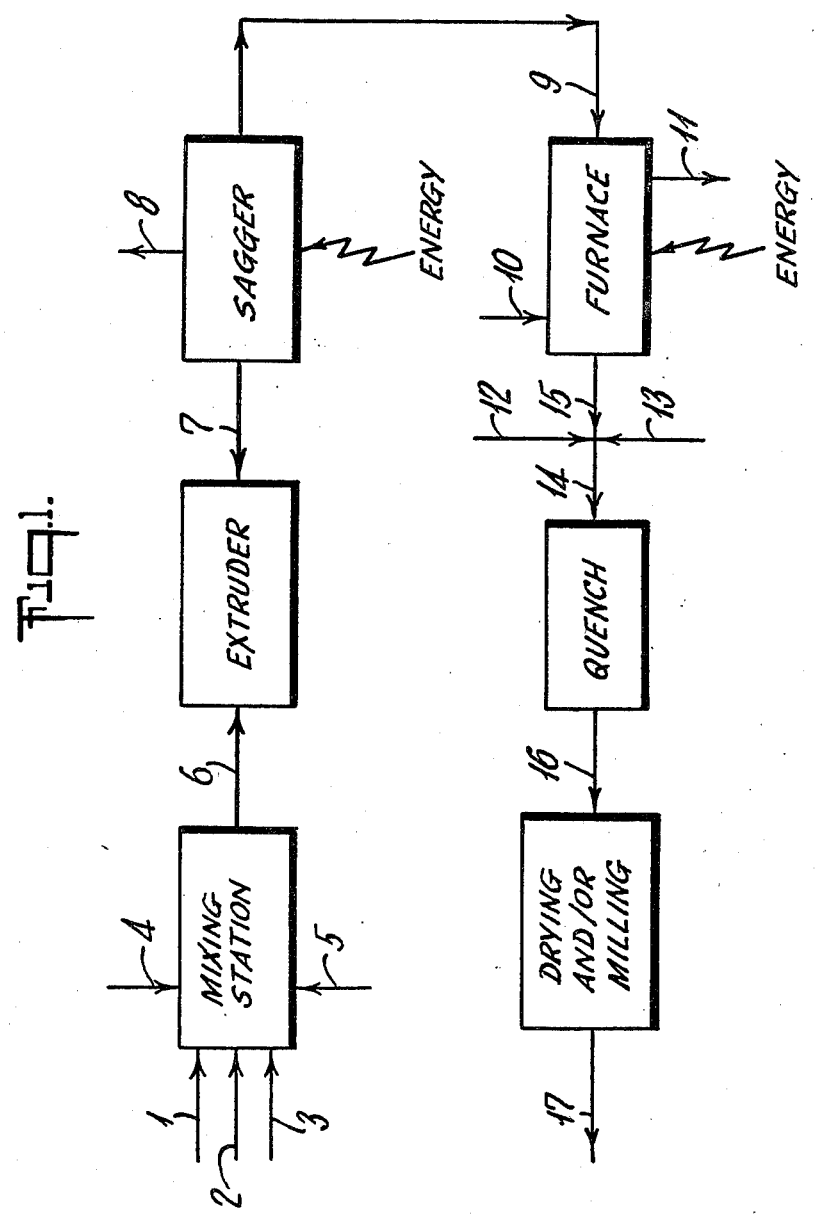

METHOD OF MAKING HIGHLY REACTIVE ION-LEACHABLE GLASS

This is a division of application Ser. No. 203,761, filed Nov. 7, 1980, now U.S. Pat. No. 4,401,773, granted Aug. 30, 1983.

BACKGROUND OF THE INVENTION

This invention relates to ion-leachable inorganic compounds in the form of glasses and suitable for use as components of cements.

Ion-leachable inorganic compounds such as the oxides of aluminum, zinc, mangesium and calcium have been intermixed with other components such as silica and formed into glasses which, when combined with such hydrogen donating compounds such as acids, will set up into a cementitious mass. The mechanism for the reaction has been described by Alan D. Wilson et al. (J. Dent. Res. 58(3), 1065–1071, March 1979) and may be represented by the generic equation.

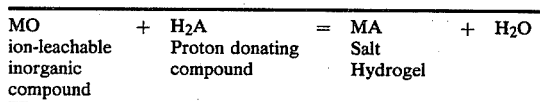

| MO | + | $H_2A$ | = | MA | + | $H_2O$ |
| ion-leachable inorganic compound | | Proton donating compound | | Salt Hydrogel | | |

Cements utilizing this mechanism have generally taken the form of glass powders incorporating the ion-leachable inorganic. These are reacted with liquid acid solutions such as aqueous carboxylic acid solutions to form a salt hydrogel structure which sets up into a hard mass. Such cement forming compositions have been suggested for use in applications such as dental cements and for orthopedic casts and splints. For example, a fluoroaluminosilicate glass powder has been suggested for use as the ion-leachable component for a dental cement in British Pat. No. 1,316,129. More recently, a similar composition has been suggested for use in orthopedic surgery in U.S. Pat. No. 4,143,018.

In using such compositions for orthopedic purposes, for example, certain criteria must be met. The composition when rendered reactive, must be capable of providing sufficient "working time", i.e., sufficient time from the start of mixing the reactants to allow the doctor time to apply and mold the cast into shape before the material reaches a stage where it is no longer malleable. Generally such times should be at most about 4 minutes and preferably from 1 to 2 minutes.

At the end of the working time period, it is most desirable that the cast set to a rock-like state as quickly as possible. While most cements, even after attaining a rock-like appearance, do not reach their ultimate strength for long periods of time, the material should reach sufficient compressive strength to allow a patient to leave the doctor's office, i.e., sufficiently hard enough to preclude deformation under expected stresses. This period is referred to as the "setting time" and should be about 6 to about 15 minutes after the cast is applied.

Within the frame work of providing practical working and setting times, perhaps the most important criterion to the user of such cements is predictability. When dealing with a patient, the orthopedist must be able to rely on the manufacturer's directions for predicting how much time he has to form a cast and when the patient will be free to leave the office.

From the foregoing it becomes apparent that a composition must be provided wherein the rate at which the salt hydrogel reaction proceeds corresponds to the constraints of working and setting times and is highly predictable and reproducible. As with most reactions, the rate is generally a factor of temperature and the availability of rate-limiting components which in this case is the availability of the leached metal ions from the powdered glass component. In practice, temperature is not generally a controlled factor in that the practitioner is accustomed to using aqueous mixture of components at essentially room temperature.

It thus becomes apparent that the manufacturer must supply a composition in which the rate of leaching of metallic ions is the controlling factor in meeting the various criteria of a satisfactory product. It is in this connection that the use of ion-leachable glass powders have heretofore been found wanting. Powders produced have varied greatly with respect to their physical and chemical homogeneity which in turn has produced erratic and unacceptable variations in working and setting times. In particular, it has been discovered that conventional glass frit making procedures have produced glass powders in which the components are separated into phases of different compositions, in which the micro-structure of the glass has been uneven, i.e., regions of amorphous material surrounding ordered regions of high crystallization, and in general, high degree of variance in amorphous to crystalline structure. While an exact correlation between rate of ion-leachability and micro-structure of glass powders is not known, reported studies have shown such a relationship between structure and rate, such being reported by T. I. Barry, et al. in J. Dent. Res. 58(3): 1072–1079, March 1979. It has been discovered from this and other work that the rate of ion-leaching is substantially decreased when the degree of crystallinity of a glass is increased.

Accordingly, there is a need for providing glass powders in which the degree of crystallinity can be reproducibly controlled and predicted.

SUMMARY OF THE INVENTION

In accordance with this invention glass is produced which is highly reactive and for which the rate of hydrogel forming reaction is both reproducible and controllable. Specifically, a shaped charge of a mixture of ion-leachable inorganic compounds is heated to form a substantially homogenous melt. The melt is next blown in a gaseous medium to form at least a partially solidified stream of thin glass fibers. The fibers then solidify and may be ground into a powder having a degree of crystallinity of less than about 1% by weight in the crystalline form.

It has been discovered that perhaps the prime factor in the variation in reactivity of various glasses is related to a corresponding variation in the degree of crystallinity. Accordingly, if this variable is essentially eliminated, the rate of reaction may be accurately controlled and predicted by simply adjusting the mixture of the inorganic components used in making the glass. It has been found that the most expedient way of eliminating the variation in crystallinity is to provide a glass to the reaction that is essentially all amorphous, i.e., has an extremely low degree of crystallinity and preferably a degree of crystallinity wherein less than about 1% by weight of the glass is in the crystalline state. In accordance with the teachings herein such a glass can be provided by performing the specific steps set out above as contrasted with conventional glass frit making processes which produce erratic and undesirable degrees of crystallinity.

Preferably, the glass fibers are formed by a compressed air stream at essentially room temperature and have a diameter which may vary from 0.004 to 0.06 mm. The homogeneity of the melted glass should be maintained as closely as is possible. To aid in homogeneity, it is important that rather than charging the mixture of inorganic components directly to the melting stage, the components first be blended and then extruded into strands or other shaped charge for the melter. Additives such as extrusion lubricants and binders may be intermixed with the inorganic components and vaporized away in a calcining step prior to charging the melter. Generally, it is sufficient to allow the glass fibers to solidify in air and the resulting product will have the low degree of crystallinity herein prescribed. It should be noted, however, that in some cases, certain glass compositions tend to crystallize very rapidly. Said in other words, crystals tend to form at temperatures very near the melt point. Such glass compositions are, for example, glasses containing MgO as a starting material. In these cases, it is preferable that solidification of the fibers be accelerated to a rate higher than mere air cooling. This can be accomplished by having the glass fibers fall directly into a water quench tank and then be dried prior to grinding.

The solidified glass in any event is ground to a powder having a particle size distribution such as to pass through a 325 mesh screen, i.e., less than 0.044 mm, with 50% being smaller than 0.015 mm in diameter. In this manner, a reactive glass powder is provided having no more than about 1% by weight in the crystalline state.

BRIEF DESCRIPTION OF THE DRAWINGS

FIG. 1 is a schematic flow diagram of a specific embodiment of the process for making glass in accordance with this invention.

DESCRIPTION OF THE PREFERRED EMBODIMENTS OF THE INVENTION

Referring now to FIG. 1, illustrated there is a schematic flow diagram of a process for producing the glass of this invention. In accordance with this invention, a shaped charge of mixture of inorganic components is homogeneously prepared, melted in a furnace, formed into solidified glass fibers, and ground into powder.

Preparing Homogeneous Mixture

The feed materials, illustrated in FIG. 1, as streams 1, 2, and 3 comprise one or more ion-leachable inorganic compounds such as the oxides of alkali, alkaline earth, aluminum, and zinc metals along with silica. The silica preferred is in the form of finely ground quartz. Aluminum, in the form of alumina, and zinc compounds are preferably introduced as powdered oxides. Alkalies and alkaline earths may be introduced in the form of carbonates. These particulate materials are thoroughly blended in a mixing station until uniform. The mixing station preferred is a Muller-type mixer.

To aid in producing a uniform feed to the furnace, it is important that the mixed inorganic compounds be fabricated into shaped forms such as, for example, extruded strands. Accordingly, additives may be introduced at the mixing station for facilitating such extrusions. In the embodiment illustrated in FIG. 1, stream 4 represents the addition of a lubricant such as the aqueous wax dispersion sold by Mobil Corporation under the tradename "Mobil Cr-C". Stream 5 represents the addition of a binder to the mixture to give the extruded product structural integrity. Such a binder may be, for example, a hydrophilic material such as ammonium alginate which is available under the tradename "Superloid" from the Kelco Company of Clark, N.J., U.S.A.

Stream 6, the mixture of ion-leachable compounds, silica, binders and lubricant is next passed to an extruder where it is extruded, at ambient temperature through a 10 mm die the produce stream 7, strands having diameters of from about 2 mm to about 15 mm.

The extruded strands, stream 7, are next charged to a sagger, i.e., a fire-clay box of the kind in which pottery is packed for firing to ovens. The sagger is heated at approximately 900° C. for about 4 hours during which time the binder and lubricant are vaporized away as well as the carbonates and water of hydration present in the inorganic feed material. These latter materials pass out of the sagger as carbon dioxide and water vapor in stream 8. This process, essentially calcination, reduces the extruded strands to a mass of friable material having substantially a homogeneous distribution of the various chemical entities.

Preparing the Melt

The calcined material, stream 9, next passes to a furnace where it is melted into molten glass. Satisfactory results have been obtained by using electric melting although other means could be employed. An electric furnace has been successfully utilized which consists of a double hulled steel shell having cooling water, streams 10 and 11, circulated between the shells. It is preferred that no refractory lining be used as such use will increase the chances for contamination and impair the homogeneity of the melt. Fortunately, it has been discovered that the batch fed to the furnace can act as its own refractory lining. Power is transmitted to the batch material in the furnace by means of two graphite electrodes.

The preferred operation sequence is to bring the electrodes together at the surface of the unmelted batch and then separate the electrodes to create an arc. The arc melts a pool of batch material adjacent to the arc. When enough molten material has been formed, the electrodes are lowered into this pool and the heating of the molten material is developed by resistance heating, without any open arc, and with heat being carried throughout the mass by conduction.

Solidifying the Melt

When sufficient melt has accumulated in the furnace, one or more streams of melt are poured from the furnace through an orifice to form melt streams having diameters from about 12 to about 25 mm, such a stream being represented in FIG. 1 by stream 15. The stream 15 is met with one or more streams of compressed air at essentially ambient temperatures, e.g., streams 12 and 13, and blown thereby into fine glass fibers. Preferably, the fine glass fibers have an average diameter of from about 0.008 to about 0.01 mm. with a maximum diameter of about 0.04 mm. The compressed air stream is at conditions of temperature and pressure and positioned relative to stream 15 in any manner such as to best produce the glass fibers described above. These conditions are functions of such factors as the particular furnace being used, the physical properties of the melt (with viscosity being the prime factor) and other factors peculiar to a specific embodiment of this invention. Typically, the compressed air stream will be at a pressure of from about 40–80 pounds per square inch, gauge, and will be placed about 25 mm from the stream 15.

If the composition of the glass mix is such as will crystallize rapidly, the air blown fibers, stream 14, are quenched immediately in a water quench, preferably by allowing them to simply fall into the quench tank. Generally, this step may be omitted provided that crystallization is not too rapid to produce the low degree of crystallinity prescribed herein. The quenched fibers, stream 16, are then passed to a drying and milling station where they are ball milled into a powder. Preferably aluminum oxide pebbles are employed in the mill and the fibers are ground to a powder which will pass through a 325 mesh screen, i.e., the largest dimension of the powder particles is less than 0.044 mm. A typical particle size distribution obtained by the process of this invention results in about 70% of the powder being less than 0.03 mm and 50% being less than 0.012 mm.

The resulting glass powder has been found to be highly reactive and almost totally amorphous. As a result, its use as a cement is totally predictable and working and setting times may be controlled.

To more specifically illustrate the advantages of this invention the following examples are given:

EXAMPLE 1

A series of glass samples are prepared by combining the following ingredients in the following proportions in a Multon-type mixer:

| Component | Moles | Weight (gms) |
|---|---|---|
| Silica | 64 | 3845 |
| Aluminum | 38.4 | 3915 |
| Calcium Carbonate | 38.4 | 3843 |

The mix is then transferred to an 8-inch diameter electric furnace of the type described above. An arc is struck at the surface of the batch between the one inch graphite electrode using 75 volts and a series resistor in the circuit. The arc starts melting the batch immediately in contact with it and when a sufficient pool is formed, the electrodes are moved down into the pool so that further melting is by conduction in the melt.

When sufficient melt has accumulated, the melt is poured as a stream through a 200 mm diameter hole in the furnace wall. The melt stream meets with an air jet at a nozzle pressure of from 40 to 80 pounds per inch gauge, said nozzle being held about 25 mm from the melt stream and at an angle of about 30 degrees to the melt stream to form the glass fibers. The air stream also serves to direct the glass fibers into a 55 gallon drum approximately half filled with water.

The fibers are collected from the drum, dried, and then placed in a ball mill containing aluminum oxide pebbles and milled overnight. The resulting powder is screened dry through a 325 mesh screen. Four batches of powder are produced in the above manner.

Each of the batches are tested for crystallinity by immersing to powder in an oil of known refractive index and observing the material through a petrographic microscope using a 45 power objective. As viewed between crossed Nicols, the crystal phase will appear light against a dark background. The percent of crystallinity for the four batches are found to be 5, 40, 15 and 25%, respectively.

Cementitious masses are made from each of the glass batches by mixing the glass powders together with the following ingredients:
1 gram glass powder
0.12 grams polyacrylic acid, molecular weight equals 154,000
0.05 grams d,l-tartaric acid (as an accelerator)
0.25 ml. water Set times are determined to be the time in which the cementitious mass hardens to the degree that the surface cannot be marred by gauging with one's fingernail. The set time for the four batches were 9, 32, 16, and 25 minutes respectively.

As can be seen from the above results, both the degree of crystallinity and the set times varied widely and unpredictably.

EXAMPLE 2

The same ingredients, in the same proportions as are set out in Example 1 above are combined in the Mueller type mixer with the exception that 1728 grams of Mobil Cr-C lubricant and 2320 gram of Superloid binder are added. The blend is then extruded at ambient temperature through a 10 mm die and the extruded strands are placed in a sagger and heated in an oven at 800°–1100° C. for four hours. The contents of the sagger are then transferred to the electric furnace described in Example 1 above, and treated in essentially the same manner.

Microscopic examinations show the glass powder to be essentially crystal free with a maximum degree of crystallinity of less than 1% by weight. The fingernail test described above is performed on cementitious masses made from batches of the glass powder and results in a substantially uniform set time of about 9 minutes.

What is claimed is:

1. A method for producing highly reactive ion-leachable glass in cementitious compositions containing proton donating compounds comprising:
   blending together a mixture of ion-leachable inorganic compounds;
   forming said blended mixture into shaped charges;
   heating said shaped charges to form a homogeneous melt;
   blowing said melt, in a gaseous medium to form at least partially solidified thin glass fibers having a degree of crystallinity of less than 1% by weight in the crystalline form and grinding the fibers.

2. The process of claim 1 wherein said gaseous medium is an air stream.

3. The process of claim 1 wherein said glass fibers have a diameter of from 0.004 to 0.06 mm.

4. The process of claim 1 wherein said shaped charges are formed by extruding said ion-leachable inorganic components into strands.

5. The process of claim 4 wherein said ion-leachable inorganic components are first blended together with extrusion lubricants prior to being formed into shaped charges.

6. The process of claim 4 wherein said ion-leachable inorganic components are first blended together with binders prior to being formed into shaped charges.

7. The process of claim 1 wherein said shaped charges are first calcined prior to being melted.

8. The process of claim 1 wherein said glass fibers are quenched by falling directly into a quench tank.

9. The process of claim 1 wherein said glass is ground to a powder having a particle size distribution such as to pass through a 325 mesh screen with 70%, by weight being smaller than 0.03 mm in diameter.

* * * * *